United States Patent
Farrell et al.

(10) Patent No.: US 12,422,887 B2
(45) Date of Patent: Sep. 23, 2025

(54) PERSONAL AREA NETWORK CONNECTION USING INTERCONNECTION LAMINATE SUBSTRATE

(71) Applicant: Human Systems Integration, Inc., Walpole, MA (US)

(72) Inventors: Brian Farrell, Walpole, MA (US); Cameron Paul Barron, Walpole, MA (US); Allan Neville, Walpole, MA (US); Richard Bernard Streeter, Walpole, MA (US); Verne Patterson, Walpole, MA (US)

(*) Notice: Subject to any disclaimer, the term of this patent is extended or adjusted under 35 U.S.C. 154(b) by 9 days.

(21) Appl. No.: 17/768,707

(22) PCT Filed: Oct. 13, 2020

(86) PCT No.: PCT/US2020/055394
§ 371 (c)(1),
(2) Date: Apr. 13, 2022

(87) PCT Pub. No.: WO2021/076503
PCT Pub. Date: Apr. 22, 2021

(65) Prior Publication Data
US 2024/0134416 A1 Apr. 25, 2024
US 2024/0231428 A9 Jul. 11, 2024

Related U.S. Application Data

(60) Provisional application No. 62/914,513, filed on Oct. 13, 2019.

(51) Int. Cl.
*G06F 1/16* (2006.01)
*A41D 1/00* (2018.01)
(Continued)

(52) U.S. Cl.
CPC ............. *G06F 1/163* (2013.01); *A41D 1/005* (2013.01); *A41D 1/04* (2013.01); *A41F 9/002* (2013.01); *H04Q 9/00* (2013.01); *H05K 3/46* (2013.01)

(58) Field of Classification Search
CPC .......... G06F 1/163; A41D 1/005; A41D 1/04; H04Q 9/00; H05K 3/46
See application file for complete search history.

(56) References Cited

U.S. PATENT DOCUMENTS

| | | |
|---|---|---|
| 4,404,460 A | 9/1983 | Kerr |
| 4,705,935 A | 11/1987 | Traffanstedt et al. |

(Continued)

FOREIGN PATENT DOCUMENTS

| | | |
|---|---|---|
| WO | WO 2008/153786 | 12/2008 |
| WO | WO 2017/013493 | 1/2017 |

(Continued)

*Primary Examiner* — Chandrahas B Patel
(74) *Attorney, Agent, or Firm* — Pandiscio & Pandiscio

(57) ABSTRACT

Disclosed embodiments describe techniques for personal area network (PAN) enablement. PAIN connection uses an interconnection laminate substrate for connectivity of personal area network components. The interconnection laminate substrate may be flexible or rigid. In one preferred form of the invention, the interconnection laminate substrate is flexible. A plurality of personal area network components is provided. An interconnection laminate substrate is provided within a manufactured article (e.g., a soft good assembly), where the interconnection laminate substrate enables connectivity among the plurality of personal area network components, and where the interconnection laminate substrate comprises interconnection wiring encapsulated in at least one protective encapsulation layer, with the interconnection wiring being coupled to a plurality of exposed connectors. At least one component of the plurality of personal area network components is plugged into at least (Continued)

one exposed connector of the plurality of exposed connectors. The interconnection laminate substrate protects interconnection wiring coupled to a plurality of exposed connectors.

68 Claims, 10 Drawing Sheets

(51) Int. Cl.
  *A41D 1/04* (2006.01)
  *A41F 9/00* (2006.01)
  *H04Q 9/00* (2006.01)
  *H05K 3/46* (2006.01)

(56) References Cited

U.S. PATENT DOCUMENTS

| | | | |
|---|---|---|---|
| 6,324,053 B1 | 11/2001 | Kamijo | |
| 6,729,025 B2 | 5/2004 | Farrell et al. | |
| 6,784,375 B2 * | 8/2004 | Miyake | H05K 3/363 |
| | | | 439/74 |
| D698,522 S | 2/2014 | Roberts et al. | |
| D698,523 S | 2/2014 | Roberts et al. | |
| D698,524 S | 2/2014 | Roberts et al. | |
| D698,525 S | 2/2014 | Roberts et al. | |
| D698,526 S | 2/2014 | Roberts et al. | |
| D698,527 S | 2/2014 | Roberts et al. | |
| D698,528 S | 2/2014 | Roberts et al. | |
| D703,416 S | 4/2014 | Roberts et al. | |
| D703,446 S | 4/2014 | Roberts et al. | |
| D703,922 S | 5/2014 | Roberts et al. | |
| D704,924 S | 5/2014 | Roberts et al. | |
| D710,084 S | 8/2014 | Roberts et al. | |
| D715,029 S | 10/2014 | Roberts et al. | |
| D715,497 S | 10/2014 | Roberts et al. | |
| 8,948,839 B1 | 2/2015 | Longinotti-Buitoni et al. | |
| D731,752 S | 6/2015 | Roberts et al. | |
| D732,273 S | 6/2015 | Roberts et al. | |
| D746,550 S | 1/2016 | Roberts et al. | |
| D754,403 S | 4/2016 | Roberts et al. | |
| 9,476,575 B2 * | 10/2016 | Hochman | F16M 11/041 |
| 9,775,396 B1 * | 10/2017 | Olivares Velasco | |
| | | | H04B 1/3833 |
| 10,201,195 B1 | 2/2019 | Khaliuta et al. | |
| 10,297,913 B2 * | 5/2019 | Khoury | H01Q 1/526 |
| 10,368,592 B2 | 8/2019 | Roh | |
| 10,820,437 B2 * | 10/2020 | Aleksov | H05K 5/065 |
| 10,934,016 B2 * | 3/2021 | Schmidt | B64D 45/00 |
| 2008/0083720 A1 | 4/2008 | Gentile et al. | |
| 2008/0287769 A1 | 11/2008 | Kurzweil et al. | |
| 2011/0108538 A1 | 5/2011 | Gray et al. | |
| 2011/0260556 A1 | 10/2011 | Partridge et al. | |
| 2012/0180184 A1 | 7/2012 | Crye | |
| 2013/0119255 A1 | 5/2013 | Dickinson et al. | |
| 2014/0070957 A1 | 3/2014 | Longinotti-Buitoni et al. | |
| 2014/0200487 A1 | 7/2014 | Ramdas et al. | |
| 2014/0318699 A1 | 10/2014 | Longinotti-Buitoni et al. | |
| 2015/0083705 A1 | 3/2015 | Cronn et al. | |
| 2015/0122791 A1 | 5/2015 | Hung et al. | |
| 2015/0136753 A1 | 5/2015 | Cronn et al. | |
| 2015/0230524 A1 | 8/2015 | Stevens et al. | |
| 2015/0313519 A1 | 11/2015 | McKenna | |
| 2015/0366504 A1 | 12/2015 | Connor | |
| 2016/0038083 A1 | 2/2016 | Ding et al. | |
| 2016/0095369 A1 | 4/2016 | Roberts et al. | |
| 2016/0135251 A1 | 5/2016 | Hopwood et al. | |
| 2016/0198776 A1 | 7/2016 | Stevens et al. | |
| 2016/0349829 A1 | 12/2016 | Spiel et al. | |
| 2017/0230916 A1 | 8/2017 | Stein et al. | |
| 2017/0325337 A1 | 11/2017 | Karagozler et al. | |
| 2017/0329365 A1 | 11/2017 | Wong et al. | |
| 2017/0332442 A1 | 11/2017 | Strecker | |
| 2018/0103694 A1 | 4/2018 | Fortenbacher | |
| 2018/0184735 A1 | 7/2018 | Longinotti-Buitoni et al. | |
| 2019/0058242 A1 | 2/2019 | Tabe | |
| 2019/0125262 A1 | 5/2019 | Markel | |
| 2019/0132948 A1 | 5/2019 | Longinotti-Buitoni et al. | |
| 2019/0208836 A1 | 7/2019 | Demers et al. | |
| 2022/0061413 A1 * | 3/2022 | Gasser | A41D 1/005 |

FOREIGN PATENT DOCUMENTS

| | | |
|---|---|---|
| WO | WO 2017/033058 | 3/2017 |
| WO | WO 2017/221204 | 12/2017 |
| WO | WO 2018/209144 | 11/2018 |
| WO | WO 2020/243189 | 12/2020 |
| WO | WO 2021/076501 | 4/2021 |

* cited by examiner

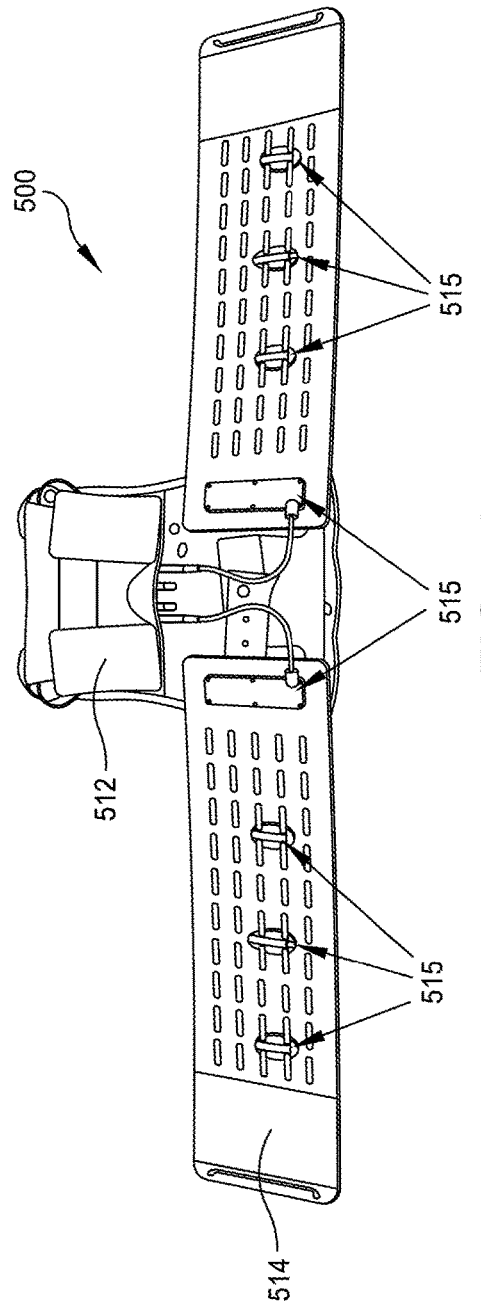
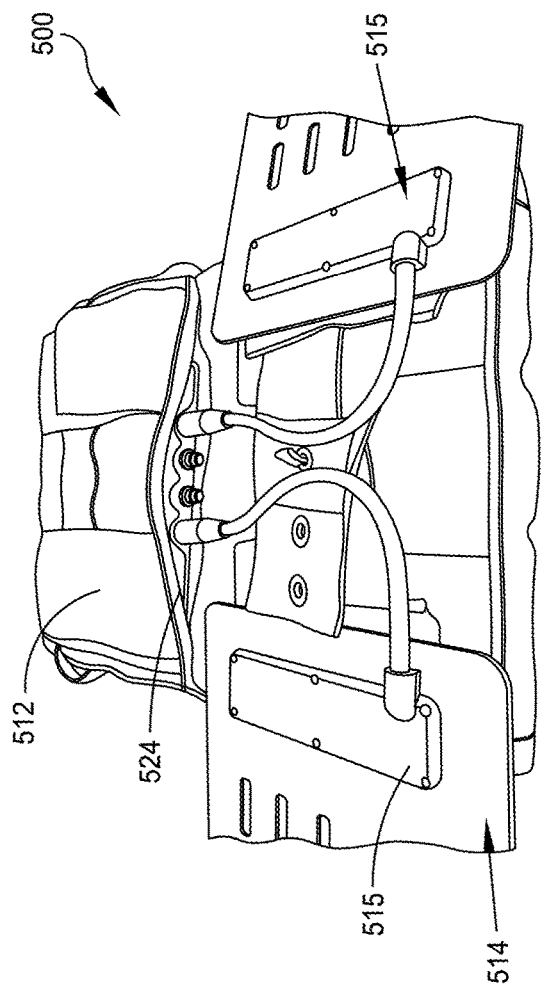

PERSONAL AREA NETWORK CONNECTION USING INTERCONNECTION LAMINATE SUBSTRATE

REFERENCE TO PENDING PRIOR PATENT APPLICATION

This patent application claims benefit of prior U.S. Provisional Patent Application Ser. No. 62/914,513, filed Oct. 13, 2019 by Human Systems Integration, Inc. and Brian Farrell et al. for PERSONAL AREA NETWORK CONNECTION USING FLEXIBLE SUBSTRATE, which patent application is hereby incorporated herein by reference.

STATEMENT REGARDING FEDERALLY SPONSORED RESEARCH OR DEVELOPMENT

This invention was made with Government support under Contract No. FA8750-18-C-0175 awarded by the Air Force Research Laboratory (AFRL) and Contract No. W91CRB-18-C-0035 awarded by the U.S. Army Program Executive Office Soldier. The U.S. Government has certain rights in this invention

FIELD OF ART

This application relates generally to personal area network (PAN) enablement, and more particularly to a personal area network connection using an interconnection laminate substrate.

BACKGROUND

People around the world live, work and play in a wide range of environments. The environments can range from the hot, arid conditions of a desert, to the hot, humid conditions of a jungle, to the frosty, low-humidity conditions of high mountains or polar regions. Whatever the environment, proper clothing is demanded for comfort, safety or even survival. The clothing that people choose to wear in their environments is often dictated by culture, local requirements, or fashion. Some cultures prescribe dress codes for what is considered proper attire for women and men, while other cultures maintain a laissez faire attitude. Similarly, light-weight, loose-fitting clothing is most comfortable in the tropics, in contrast to the heavy wool or fleece sweaters and jackets in cold climates. In terms of fashion, wearing a couture gown and extravagant jewelry, or wearing a black tie and a diamond-accented dress watch, may be highly appropriate for a red carpet or a gala affair, although such attire would be ludicrous or even dangerous in the Antarctic. People thus choose and wear their clothing to meet these many diverse requirements. In many cases, the clothing choices come down to personal preference, clothing price point, or even individual sense of fun. An otherwise drab or muted outfit can be enlivened by a colorful scarf, a brightly patterned shirt, or a particularly loud tie.

SUMMARY

Novel personal area network enablement is based on using an interconnection laminate substrate to which personal area network components can be connected. This interconnection laminate substrate may be flexible or rigid. In the preferred form of the invention, the interconnection laminate substrate is flexible. The interconnection laminate substrate comprises layers for shielding, power distribution, communication, and so on. The interconnection laminate substrate can include a protective encapsulation layer. The protective encapsulation layer may be flexible or rigid. In a preferred form of the invention, the protective encapsulation layer is flexible. The protective encapsulation layer may comprise a polymer. One or more personal area network components can be plugged into one or more exposed connectors, where the exposed connectors are coupled to the interconnection laminate substrate. The interconnection laminate substrate further enables communication between or among PAN components, provides power to the PAN components, etc. The powering of the PAN components is accomplished using a battery, a power scavenging source, and so on. The powering of the one or more PAN components can be controlled by power management. The power management can be based on an algorithm, a power usage policy, power usage history, user selection, etc. The power management can enable or disable power to PAN devices based on previous usage, can provide recommendations for powering up or powering down devices, and the like. The power management can further protect personal area network components and interconnects during over-voltage or over-current conditions.

In embodiments, a method for providing a personal area network connection comprises: providing a plurality of personal area network components; providing an interconnection laminate substrate within a manufactured article (e.g., a soft good assembly), wherein the interconnection laminate substrate enables connectivity among the plurality of personal area network components, and wherein the interconnection laminate substrate encapsulates interconnection wiring coupled to a plurality of exposed connectors; and connecting at least one component of the plurality of personal area network components to at least one exposed connector of the plurality of exposed connectors.

In other embodiments, an apparatus for personal area network enablement comprises: a plurality of personal area network components; an interconnection laminate substrate within a manufactured article (e.g., a soft good assembly), wherein the interconnection laminate substrate enables connectivity among the plurality of personal area network components, and wherein the interconnection laminate substrate encapsulates interconnection wiring coupled to a plurality of exposed connectors; at least one exposed connector of the plurality of exposed connectors connected to at least one component of the plurality of personal area network components; and at least one additional exposed connector of the plurality of exposed connectors connected to a power source.

In one form of the invention, there is provided a method for personal area network enablement, the method comprising:

providing a plurality of personal area network components;

providing an interconnection laminate substrate within a manufactured article, wherein the interconnection laminate substrate enables connectivity among the plurality of personal area network components, and wherein the interconnection laminate substrate comprises interconnection wiring encapsulated in at least one protective encapsulation layer, with the encapsulated interconnection wiring being coupled to a plurality of exposed connectors; and connecting at least one component of the plurality of personal area network components into at least one exposed connector of the plurality of the exposed connectors.

In another form of the invention, there is provided apparatus for personal area network enablement, the apparatus comprising:

a plurality of personal area network components; and an interconnection laminate substrate within a manufactured article, wherein the interconnection laminate substrate enables connectivity among the plurality of personal area network components, and wherein the interconnection laminate substrate comprises interconnection wiring encapsulated in at least one protective encapsulation layer, with the encapsulated interconnection wiring being coupled to a plurality of exposed connectors;

wherein a first of the plurality of personal area network components is connected to a first of the plurality of exposed connectors, and a second of the plurality of personal area network components is connected to a second of the plurality of exposed connectors.

Various features, aspects, and advantages of various embodiments will become more apparent from the following further description.

BRIEF DESCRIPTION OF THE DRAWINGS

The following detailed description of certain embodiments may be understood by reference to the following figures wherein:

FIGS. 5A and 5B show an example tactical personal area network which includes a cummerbund.

DETAILED DESCRIPTION

Figure 1:
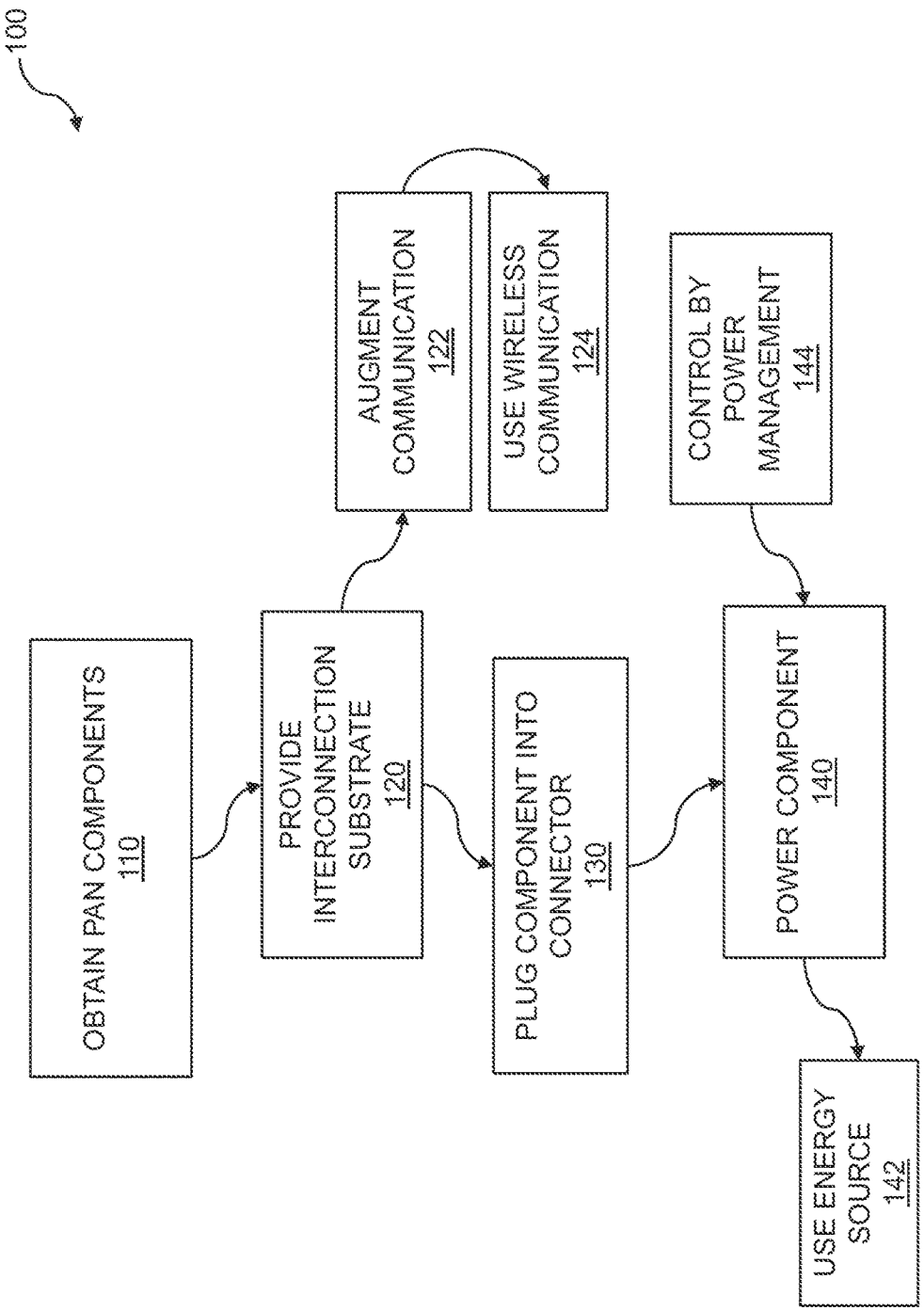
FIG. 1 is a flow diagram for personal area network (PAN) connection using an interconnection laminate substrate.

Civilians, emergency services personnel, first responders, law enforcement personnel, and military personnel typically carry devices that are required for daily activities, emergency response, combat, and so on. These devices can include communications devices, navigation units, imaging devices, and the like. Each of these devices requires power, and many of the devices require access to some type of communications channel. The situation is particularly acute for military personnel whose kit can include multiple radios, video equipment, a GPS or navigation unit, sighting and ranging units, etc. In addition, emerging requirements can include equipment for biometric measurements for soldiers, augmented reality equipment, heating units such as heated gloves, feedback devices which provide information such as haptic feedback, gesture control devices, and more. Traditionally, the electronic equipment carried by a solder might be coupled to battery packs, to antennas, or to other equipment, using cables. The cables have posed many problems because they often impede the movement of the person carrying the equipment. The cables could be easily snagged or broken by other equipment, objects within the environment, etc. Further, every device that is "powered on" consumes energy. Without some plan for energy conservation, and an awareness of what equipment is needed at any given time, battery power can be easily exhausted before the end of a mission.

Being draped in cables, or running out of power for electronic devices plugged into the cables, is at least inconvenient and at worst life threatening. To reduce the need for battery cables, the one or more electronic devices can be plugged into an interconnection laminate substrate. The interconnection laminate substrate can provide power to the electronic devices, shielding for signals that are communicated between or among the electronic devices, and so on. In addition, some "intelligence" can be introduced into the powering of the electronic devices, i.e., in the form of power management. The power management can power up or power down devices based on historical usage, can put devices into low power mode when not in use, and so on. Power management can make recommendations about which devices to power up or to power down. Further, power management can capture or "scavenge" energy. The scavenged energy can be converted and stored in batteries and later used to power the electronic devices. The interconnection laminate substrate can also provide protection, where the protection can include mechanical, environmental, or shielding purposes. The shielding purposes can include electromagnetic interference resilience, signal shielding, and the like. In one form of the invention, a plurality of personal area network components is provided, and an interconnection laminate substrate is provided within a manufactured article (e.g., a soft good assembly). The manufactured article can include a vest, a cummerbund, and so on. The interconnection laminate substrate enables connectivity among the plurality of personal area network components, and the interconnection laminate substrate encapsulates interconnection wiring coupled to a plurality of exposed connectors. At least one component of the plurality of personal area network components is plugged into at least one exposed connector of the plurality of exposed connectors. The interconnection laminate substrate provides and manages power to the components.

FIG. 1 is a flow diagram for a personal area network (PAN) connection using an interconnection laminate substrate, which may be flexible or rigid. In the preferred form of the invention, the interconnection laminate substrate is flexible. People frequently carry electronic devices with them as they are going about their daily lives. Smartphones are extremely popular since these devices provide communications capabilities such as telephony, text, and email; imaging capabilities such as video and images; location capabilities such as GPS; and many other features. The capabilities of these smartphones are further enhanced through the downloading of "apps". People may also carry other devices such as PDAs or tablets, computing devices such as laptops, digital cameras, and so on. If a person is concerned about whether she or he has sufficient battery power for their electronic devices to operate throughout their busy day, that person can carry a charger, cables, a battery, and so on. The person may also choose to carry a small solar panel for a backup recharge on a sunny day. The person quickly notices, however, that operating and charging devices while "on the go" can be inconvenient or impossible.

The difficulty of powering electronic devices and enabling communications for those devices is far more complicated for professionals or military personnel who are routinely required to carry many more electronic devices than a mere smartphone. The electronic devices can include communications equipment, video equipment, sophisticated navigational equipment, and so on. Further, such professionals or military personnel may be required to carry additional equipment such as biometric sensors, augmented reality equipment, haptic devices, gesture control devices, and so on. The professionals and military personnel may also carry and use heated garments such as heated gloves. Simply plugging all of these devices into batteries and cables is not viable for the simple reasons that (i) the cables would be obstructive, and (ii) the battery power would quickly be exhausted. Instead, the electronic components can be interconnected using a personal area network (PAN). A PAN enables communication between and among the electronic devices, powering of the devices, and so on. Connections to the PAN can be enabled using an interconnection laminate substrate. By adding some "intelligence" to the capabilities of the interconnection laminate substrate, power management can be enabled. Power management can be used to supply power to electronic devices that require the power at a given time. The power management can be further used to control power draw from a battery and thereby extend the runtime for the battery.

As seen in FIG. 1, the flow 100 includes providing a plurality of personal area network components 110. The PAN components can include various electronic devices, where the electronic devices can address a wide range of applications. The PAN components can include communications components. The communications components can include analog or digital radios, satellite radios, encrypted radios, and so on. More than one communication component can be included. The communication components can comprise components for networking such as wireless networking. The wireless networking can include Wi-Fi™, Bluetooth™ infrared (IR), Zigbee, and the like. The PAN components can include video components. The video components can capture video, still images, and so on. The video components can include visible light components, near-infrared components, night vision components, etc. The PAN components can include navigation components such as GPS location components. The PAN components can include "call for fire" components, where the call for fire components can include GPS coordinates, ranging information, direction, velocity, etc. The call for fire component can include "target painting" capabilities. The PAN components can include power sources. A power source can include a battery such as a sealed lead acid battery, a lithium-ion battery, a lithium-iron-phosphate battery, and so on. In embodiments, the battery can include a conformable wearable battery, i.e., a wearable battery where the shape of the battery can conform to its surroundings (e.g., to conform to the shape of a torso, to conform to the shape of a backpack, etc.). Other power sources could include power from a vehicle which is ridden by the user or power from one of the attached devices that have their own independent power source. The power source can further include a power scavenging source. The power scavenging source can capture energy, convert the energy to electrical energy, and store the electrical energy in a battery. In embodiments, the power scavenging source can derive energy from solar power, body motion, or body heat. The derived energy can be used immediately or stored for later use. In other embodiments, the interconnection laminate substrate can provide a modular interface that allows multiple configurations of connectors and electronics. The multiple configurations can support different form factors, power requirements, garment restrictions, etc. In embodiments, the interface can be part of the interconnection laminate substrate.

The flow 100 includes providing an interconnection laminate substrate 120 within a manufactured article (e.g., a soft good assembly). The interconnection laminate substrate can comprise a plurality of layers, where the layers can include shielding layers, flexible layers, communicating layers, power and ground layers, etc. The interconnection laminate substrate can enable connectivity among the plurality of personal area network components. The interconnection laminate substrate can encapsulate interconnection wiring coupled to a plurality of exposed connectors. In embodiments, the interconnection laminate substrate comprises a protective encapsulation layer. The protective encapsulation layer may be flexible or rigid. In a preferred form of the invention, the protective encapsulation layer is flexible. The protective encapsulation layer may comprise a polymer. This polymer may be a thermoplastic. The protective encapsulation layer may comprise a woven thermoplastic. In the preferred form of the invention, the woven thermoplastic provides an environmental seal, can be sewn to, can be drilled through or bolted to, etc. In one preferred form of the invention, the woven thermoplastic comprises a Tegris® woven thermoplastic composite made by Milliken Textiles of Spartanburg, SC. The woven thermoplastic can be strong, flexible, heat resistant, and so on. The interconnection laminate substrate can include circuitry, including flexible circuitry, and including encapsulated flexible interconnection wiring. The flexible circuitry can include one or more flexible circuit boards, where the flexible circuit boards can include power and ground traces, signal traces, circuitry, etc. In some embodiments, the flexible circuitry can be laminated between layers of the protective encapsulation layer, e.g., the woven thermoplastic.

The manufactured article (e.g., a soft good assembly) can be situated within pieces of equipment. The manufactured article (e.g., a soft good assembly) can be situated in a garment, where the garment can include a vest. In embodiments, the manufactured article (e.g., a soft good assembly) can include a vest, a belt, a rucksack, a helmet, or a seat. In embodiments, the interconnection laminate substrate is flexible. The flexible interconnection laminate substrate facilitates adding the flexible interconnection laminate substrate to the manufactured article (e.g., a soft good assembly such as a garment or a piece of equipment), placing the flexible interconnection laminate substrate within the manufactured article (e.g., a soft good assembly such as a garment or a piece of equipment), and the like. In embodiments, the flexible interconnection laminate substrate can be situated in a backpack, including mounted to the backpack or incorporated into the material of the backpack. The flexible interconnection laminate substrate can be sufficiently flexible to enable the flexible interconnection laminate substrate to be wrapped around a body part. In embodiments, a garment incorporating the flexible interconnection laminate substrate can wrap the flexible interconnection laminate substrate around the torso of a wearer. The flexible interconnection laminate substrate can be included in an arm wrap, a leg wrap, and the like. In other embodiments, the garment carrying the flexible interconnection laminate substrate can include a cummerbund.

In embodiments, the personal area network components can include one or more body sensors. The body sensors can be used to monitor biometric characteristics associated with a user of the body sensors. In embodiments, the body sensors can include a blood oxygen sensor, an orientation sensor, an acceleration sensor, a heart rate sensor, or a body temperature sensor. The body sensors can be used to determine health and welfare of the person using the sensor. The body sensors can be used to determine a "soldier down" situation. The flow 100 further includes augmenting communication between the at least one component of the plurality of personal area network components and an additional personal area networking component (step 122). The augmenting step 122 can be accomplished using wireless communications (step 124). As discussed herein, the wireless communications can include Wi-Fi™, Bluetooth™, infrared, etc. In embodiments, the additional personal area networking component can also be coupled to the interconnection laminate substrate using a wired coupling. The wired coupling can be used to provide power and power management to a PAN component. In some embodiments, the additional personal area networking component can have only wireless connectivity to the at least one component of the plurality of personal area networking components. The wireless connectivity can be used for data exchange, command and control, etc. In some embodiments, the interconnection laminate substrate can enable the plurality of personal area network components to provide command, control, or communication (CCC) capabilities.

The flow 100 includes plugging at least one component of the plurality of personal area network components into at least one exposed connector (step 130) of the plurality of exposed connectors associated with the interconnection laminate substrate. These exposed connectors can be mounted on the interconnection laminate substrate, coupled to the interconnection laminate substrate, and so on. In embodiments, the exposed connectors can include a cable. The cable can comprise one or more twisted pairs, a shielded cable, a coaxial cable, a ribbon cable, and so on. In embodiments, the interconnection laminate substrate can protect interconnection wiring coupled to a plurality of exposed connectors. The protected interconnection wiring can be protected against over-voltage, over-current, crosstalk, inadvertent transmission of signals, etc. In other embodiments, the interconnection laminate substrate provides protection for mechanical, environmental, or shielding purposes. The protection can include strain relief for the cables, environmental coatings, signal shielding, etc.

In one form of the invention, the interconnection laminate substrate comprises one or more protective encapsulation layers which protect encapsulated interconnection wiring from environmental hazards and one or more electromagnetic interference (EMI) protective layers which protect the encapsulated interconnection wiring from EMI, with the encapsulated interconnection wiring being connected to exposed connectors (i.e., connectors which are not encapsulated in the interconnection laminate substrate).

The flow 100 further includes powering the at least one component 140, where the powering is enabled by plugging the at least one component into an exposed connector. As discussed herein, the powering can include providing a battery source, where the battery is attached to the interconnection laminate substrate. The powering can include an energy scavenging source. In embodiments, the powering can use an energy source (step 142) plugged into the interconnection laminate substrate. More than one energy source can be plugged into the interconnection laminate substrate. In the flow 100, the powering can be controlled by power management (step 144). The power management can be effected based on a code, an algorithm, a heuristic, and so on, where the code, algorithm, or heuristic can be executed on a processor device. In the flow 100, the power management can enable or disable power to devices based on previous usage. The previous usage can include historical usage such as minimal or no usage of a component (e.g., lighting during the day), previous usage on the current mission, etc. The power management can be based on a policy or a priority. In other embodiments, the power management can provide recommendations for device power on or power off. The recommendations can be based on a priority, a policy, or a state of battery charge; time since last use; etc. In further embodiments, the power management can protect personal area network components, the interconnection wiring and/or the exposed connectors during over-voltage or over-current conditions. Such conditions could occur due to natural causes such as a lightning storm, man-made causes such as an electromagnetic pulse (EMP), and so on. Such conditions could occur as a result of equipment failure, power source failure, and the like. Various steps in the flow 100 may be changed in order, repeated, omitted, or the like without departing from the disclosed concepts. Various embodiments of the flow 100 can be included in a computer program product embodied in a non-transitory computer readable medium that includes code executable by one or more processors. Other embodiments of the flow 100 can include an apparatus.

Figure 2:
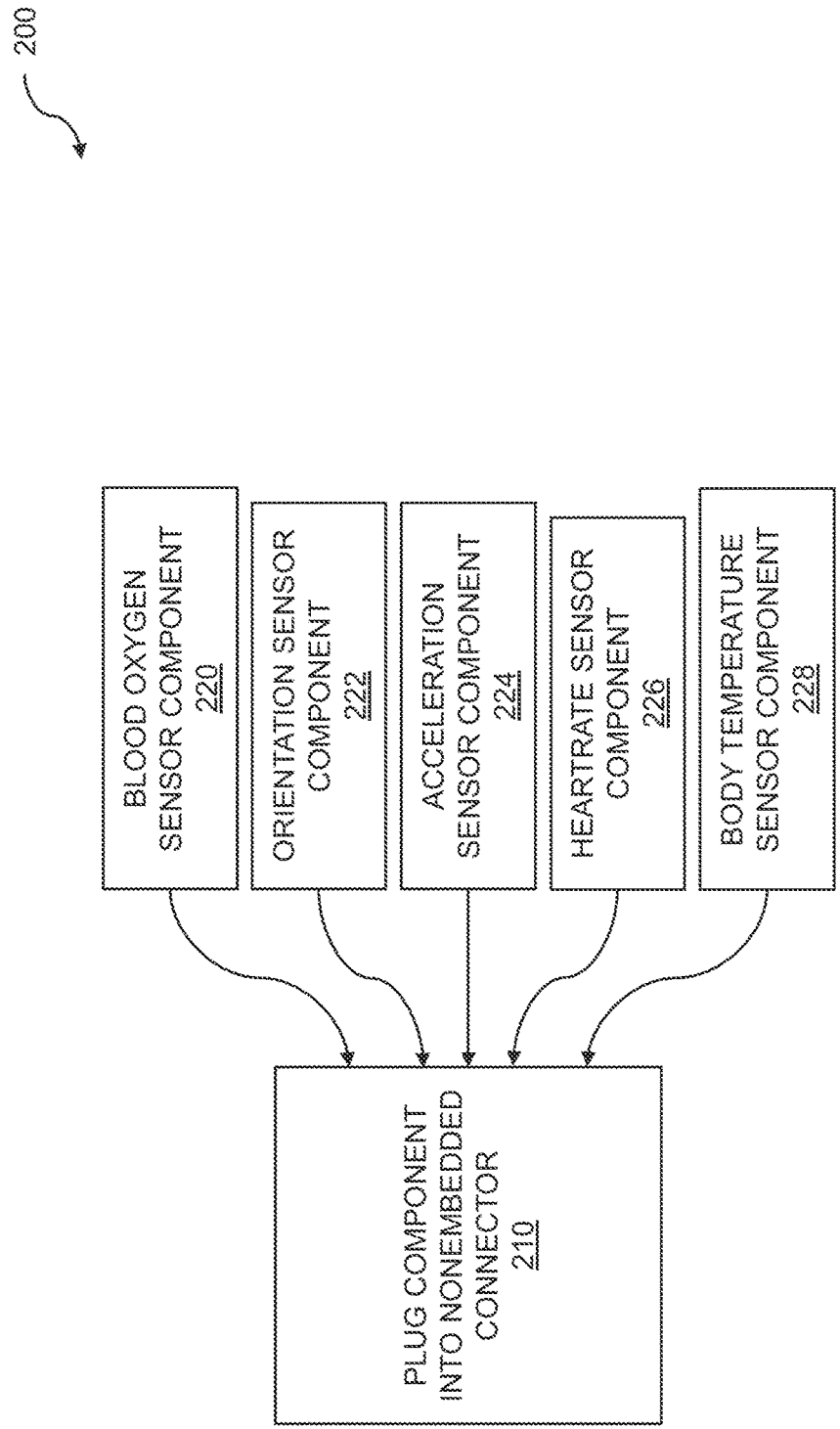
FIG. 2 is a flow diagram for sensor use.

FIG. 2 is a flow diagram for sensor use. As discussed herein, personal area network components can be connected to an interconnection laminate substrate. The interconnection laminate substrate may be flexible or rigid. In the preferred form of the invention, the interconnection laminate substrate is flexible. The interconnection laminate substrate can provide power, communications capabilities, and so on. The PAN components can include components that can support analog, digital, encrypted or other communications; video or other imaging; location such as GPS location, virtual or augmented reality; garment heating; haptic feedback; gesture control; and the like. The PAN components can further include sensors for measuring biometric data. PAN components, including biometric sensors, can be enabled by a personal area network connection using an interconnection laminate substrate. In one form of the invention, a plurality of personal area network components is provided. An interconnection laminate substrate within a manufactured article (e.g., a soft good assembly) is provided, where the interconnection laminate substrate enables connectivity among the plurality of personal area network components, and where the interconnection laminate substrate comprises encapsulated interconnection wiring coupled to a plurality of exposed connectors. At least one component of the plurality of personal area network components is plugged into at least one exposed connector of the plurality of exposed connectors.

The flow 200 includes plugging at least one component of the plurality of personal area network components into at least one exposed connector of the plurality of exposed connectors (step 210). The exposed connector can include a consumer off-the-shelf (COTS) connector, an industry standard connector, a proprietary connector, a military standard connector, and so on. The exposed connector can be mounted to the interconnection laminate substrate (e.g., by incorporating a portion of the exposed connector in the protective encapsulation layer, bolting or sewing the exposed connector to the protective encapsulation layer, etc.), coupled to the interconnection laminate substrate using a pigtail, etc. Thus, it will be appreciated that the exposed connectors can be fixedly mounted to the interconnection laminate substrate (e.g., by incorporating a portion of the exposed connector in the protective encapsulation layer, bolting or sewing the exposed connector to the protective encapsulation layer, etc.) or the exposed connectors can be movably mounted to the interconnection laminate substrate (e.g., by using a pigtail configuration). In embodiments, the exposed connectors include a cable. The cable can include a multiconductor cable, a twisted pair cable, a shielded cable, and the like. As discussed herein, the PAN component can include a sensor for detecting biometric data. The flow 200 includes using a blood oxygen sensor component (step 220). A blood oxygen sensor, such as a pulse oximeter, can indirectly determine blood oxygen levels based on absorption of light. The flow 200 can include using an orientation sensor component (step 222). The orientation of a user can be determined using magnetometers. The magnetometers can be included within a component such as an inertial measurement unit (IMU).

The flow 200 includes using an acceleration sensor component (step 224). The acceleration sensor component can detect vertical or horizontal acceleration, rotational acceleration, and so on. The acceleration can be determined using one or more accelerometers. In embodiments, the one or more accelerometers can be included within the IMU. The acceleration sensor can be used to detect a fall or inactivity. The flow 200 includes using a heart rate sensor component (step 226). The heart rate sensor can be used to determine heart rate, changes in heart rate, heart rate variability, and so on. The heart rate sensor can include an electrical sensor, an optical sensor, and the like. The flow 200 includes using a body temperature sensor component (step 228). The body temperature sensor can be used to determine skin temperature, core temperature, and so on. Body temperature can be inferred by techniques such as measuring skin temperature. Body temperature can be measured using inserted or ingested sensors. Various steps in the flow 200 may be changed in order, repeated, omitted, or the like without departing from the disclosed concepts. Various embodiments of the flow 200 can be included in a computer program product embodied in a non-transitory computer readable medium that includes code executable by one or more processors.

Figure 3:
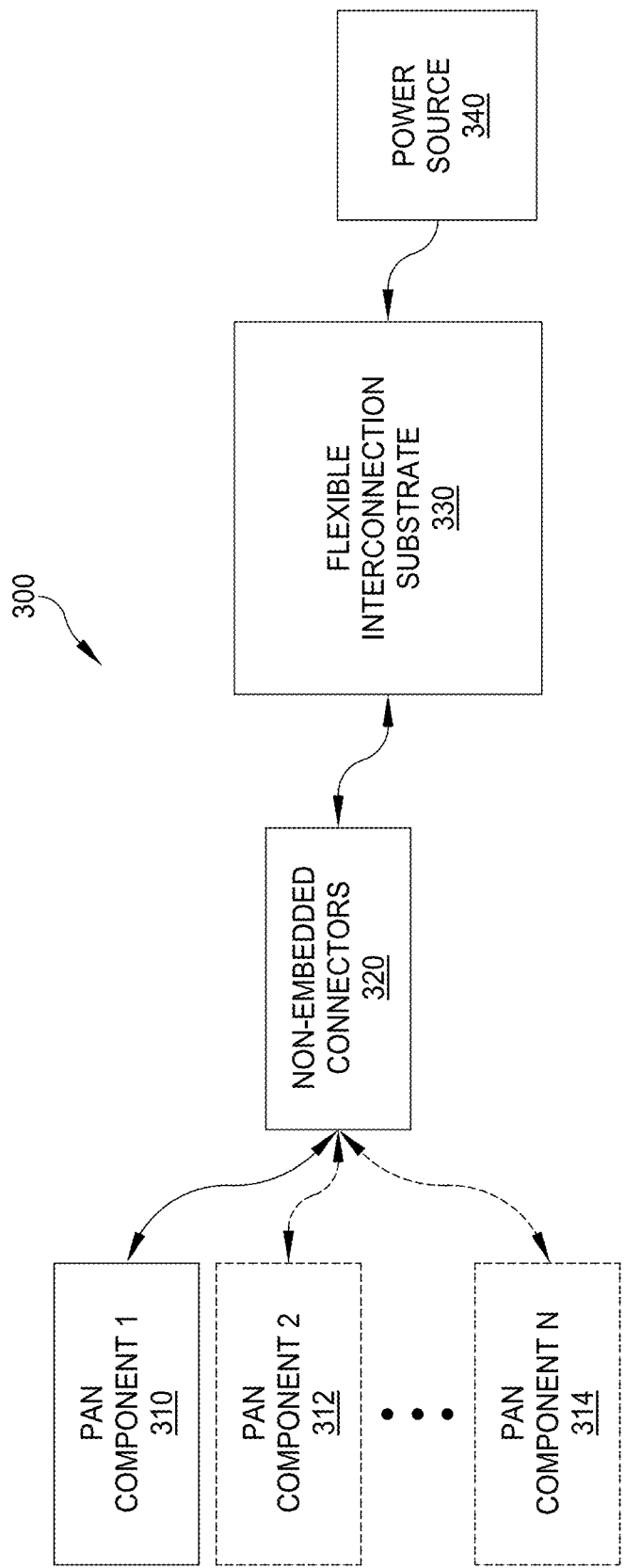
FIG. 3 shows a PAN tray using an interconnection laminate substrate.

FIG. 3 shows a PAN tray using an interconnection laminate substrate. The interconnection laminate substrate may be flexible or rigid. In the preferred form of the invention, the interconnection laminate substrate is flexible. A variety of electronic devices can be used by an individual for purposes including health and safety, law enforcement, national defense, and so on. These electronic devices require power to operate, and in some cases, must be in communication with each other or with further electronic devices that can be located remotely. For safety, reliability, or other purposes, the electronic devices can be mounted onto or within a manufactured article (e.g., a soft good assembly, where the soft good assembly can include a vest, a cummerbund, and so on). The manufactured article can further include a rucksack or backpack, a helmet, or a seat. Instead of attempting to provide power and interconnections between and among PAN components using individual cables, an interconnection laminate substrate can be used. The interconnection laminate substrate can be part of the manufactured article (e.g., a soft good assembly). Personal area network connection is enabled using an interconnection laminate substrate.

A PAN tray using an interconnection laminate substrate is shown at 300. The interconnection laminate substrate can provide power, communications, and so on, to one or more PAN components. The PAN components can include PAN component 1 310, PAN component 2 312, PAN component N 314, and so on. While three PAN components are shown in FIG. 3, other numbers of PAN components can be coupled to the interconnection laminate substrate. The PAN components can include components for communication, location, biometrics, video, augmented or virtual reality, and so on. Other components such as end user components (not shown) can be coupled to the interconnection laminate substrate. The end user components can include computing devices such as a laptop computer; personal or consumer electronic components such as smartphones, tablets, or PDAs; and so on. The one or more PAN components, end user components, and so on, can be connected to exposed connectors 320. The exposed connectors are connected to the interconnection wiring encapsulated in the interconnection laminate substrate. The exposed connectors can include standard connectors such as connectors for consumer devices, industry standard connectors, military standard connectors, proprietary connectors, and so on. In embodiments, the exposed connectors include a cable.

The exposed connectors, cables, and so on, are coupled to the encapsulated interconnection wiring of an interconnection laminate substrate 330. The interconnection laminate substrate can be incorporated into or placed into a garment, a piece of equipment, and so on. In embodiments, the garment can include a vest. The vest can include an article of clothing, a piece of equipment such as a tactical vest, and so on. In embodiments, the garment wraps the interconnection laminate substrate around the torso of a wearer. The interconnection laminate substrate can be worn under other garments, over other garments, etc. In embodiments, the garment can include a cummerbund.

The interconnection laminate substrate can be constructed from a variety of materials. In embodiments, the interconnection laminate substrate comprises one or more protective encapsulation layers, e.g., a woven thermoplastic. The interconnection laminate substrate can include a plurality of layers, where the plurality of layers can include conducting layers, insulating layers, shielding layers, etc. The one or more protective encapsulation layers preferably encapsulate the other components (e.g., layers) of the interconnection laminate substrate so as to environmentally protect those components. In a preferred form of the invention, the woven thermoplastic can be sewn to, can be drilled through or bolted to, etc. In one preferred form of the invention, the woven thermoplastic comprises a Tegris® thermoplastic composite made by Milliken Textiles of Spartanburg, SC.

The interconnection laminate substrate can be coupled to a power source 340. The power source can include a battery, a power scavenging source, and so on. The power source can be part of a vest, a cummerbund, a backpack or rucksack, and so on. The batteries can include sealed lead acid (SLA) batteries, lithium-ion batteries, nickel metal hydride batteries, lithium iron phosphate (LiFePO4) batteries, etc. In embodiments, the battery can include a conformable wearable battery, i.e., a wearable battery where the shape of the battery can conform to its surroundings (e.g., to conform to the shape of a torso, to conform to the shape of a backpack, etc.). The scavenging power source can obtain power from a variety of sources. In embodiments, the power scavenging source can derive energy from solar power, body motion, or body heat.

Figure 4A:
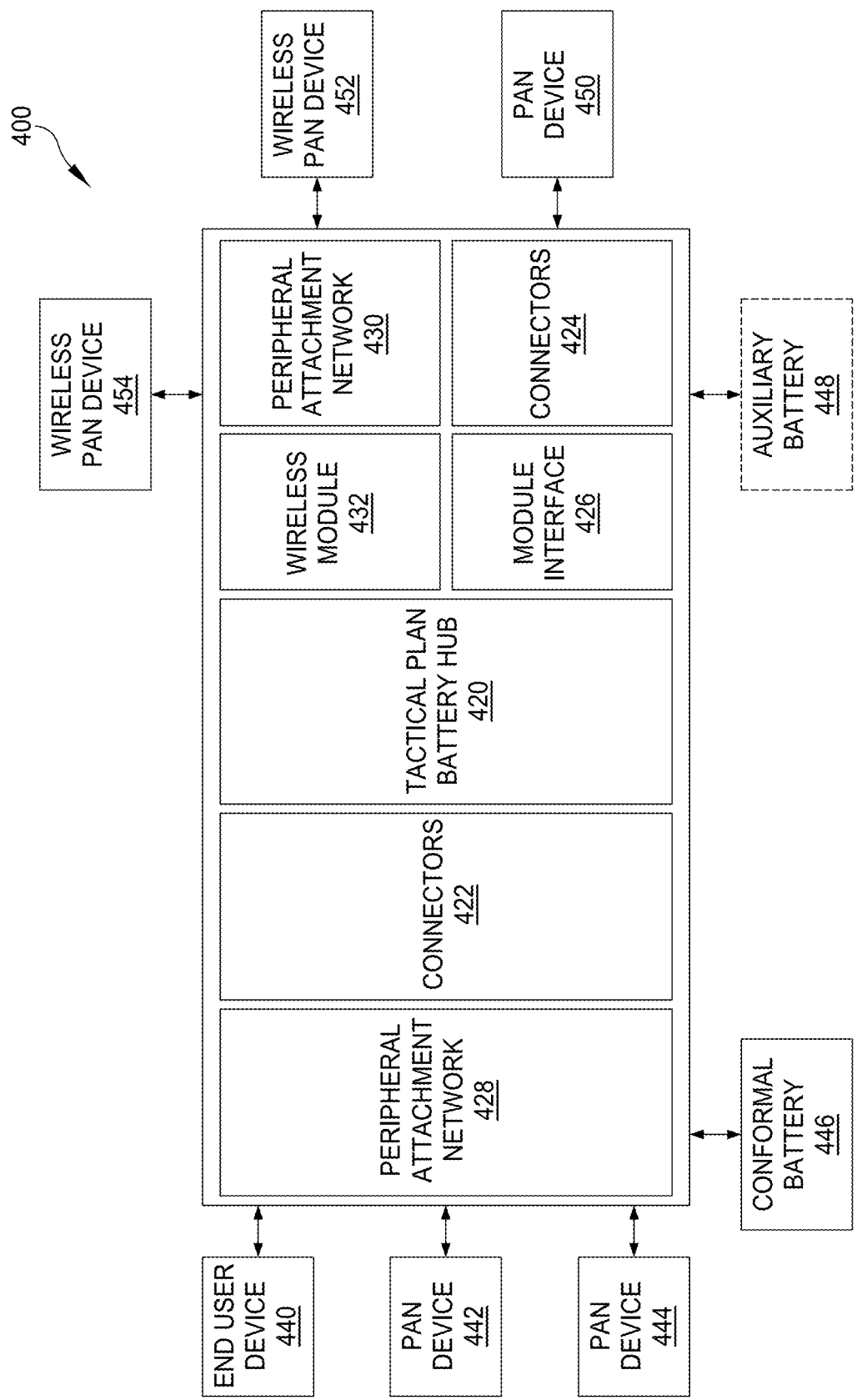
FIG. 4A illustrates a tactical PAN block diagram.

FIG. 4A illustrates a tactical PAN block diagram. A personal area network, sometimes also called a body area network, can provide connections for power, communications, control, management, and so on, to a variety of personal area network components. The personal area network connections can be accomplished using an interconnection laminate substrate. The interconnection laminate substrate may be flexible or rigid. In the preferred form of the invention, the interconnection laminate substrate is flexible. In one form of the invention, a plurality of personal area network components can be provided. An interconnection laminate substrate can be provided within a manufactured article (e.g., a soft good assembly), where the interconnection laminate substrate enables connectivity among the plurality of personal area network components, and where the interconnection laminate substrate comprises encapsulated interconnection wiring coupled to a plurality of exposed connectors. At least one component of the plurality of personal area network components is plugged into at least one exposed connector of the plurality of exposed connectors. The PAN can be used for a variety of applications including commercial, health and safety, law enforcement, military, etc.

In one form of the invention, the interconnection laminate substrate comprises one or more protective encapsulation layers which protect encapsulated interconnection wiring from environmental hazards and one or more electromagnetic interference (EMI) protective layers which protect the encapsulated interconnection wiring from EMI, with the encapsulated interconnection wiring being connected to exposed connectors (i.e., connectors which are not encapsulated in the interconnection laminate substrate).

A tactical PAN block diagram is shown at 400. The tactical PAN can include a hub 410, where the hub can be based on a wearable soft good such as a vest or a cummerbund. The tactical PAN hub can include a tactical PAN battery hub 420. The tactical PAN battery hub can select a power source such as a battery or a power scavenging source, can manage power provisioning to a PAN component such as a radio or a GPS, can enable or disable power to a PAN component based on previous usage, and so on. The hub 410 can include exposed connectors 422. The exposed connectors can be used to connect further hub components to the hub, to couple PAN devices to the hub, to couple power sources, and so on. The hub 410 can further include additional exposed connectors 424. The additional exposed connectors can be used to couple components, modules, etc. for peripheral attachment to the hub. The hub can include a module interface 426. The module interface can be used to provide interconnection, communication, etc., between modules and the hub. The module interface can couple the hub to one or more networks, such as peripheral attachment network 428, and peripheral attachment network 430. The peripheral attachment networks 428, 430 can utilize the aforementioned interconnection laminate substrates to electrically interconnect the various devices (components) of the peripheral attachment networks (i.e., via the encapsulated interconnection wiring and exposed connectors of the interconnection laminate substrates). The peripheral attachment networks 428, 430 can be based on various network protocols or techniques such as a universal serial bus (USB), an advanced extensible interface (AXI), packet switching such as X.25, and so on. In embodiments, the hub can be coupled to a wireless module 432. The wireless module can be used to facilitate communication with a PAN component using a wireless protocol such as Wi-Fi™, Bluetooth™, Zigbee™, etc.

The hub 410 can be coupled to a variety of components using exposed connectors, cables, wireless links, and so on. In embodiments, the hub can be coupled to an end user device 440. The end user device can include a computing device such as a laptop computer. The hub can be coupled to a personal electronic device such as a PDA, smartphone, or tablet; a storage device such as a flash storage device; and the like. The tactical hub can be coupled to one or more PAN devices. In embodiments, the PAN devices, such as pan device 442, pan device 444, and pan device 450, can include various types of components. The components can include communications, navigation, video, biometric, augmented reality, or other components. The hub 410 can be coupled to one or more power sources. In embodiments, the hub can be coupled to a conformable wearable battery 446. The hub can be coupled to a further power source such as auxiliary battery 448, a power scavenging source (not shown), and the like. In further embodiments, the hub can be coupled to one or more wireless PAN devices such as wireless PAN device 452, wireless PAN device 454, and so on.

Figure 4B:
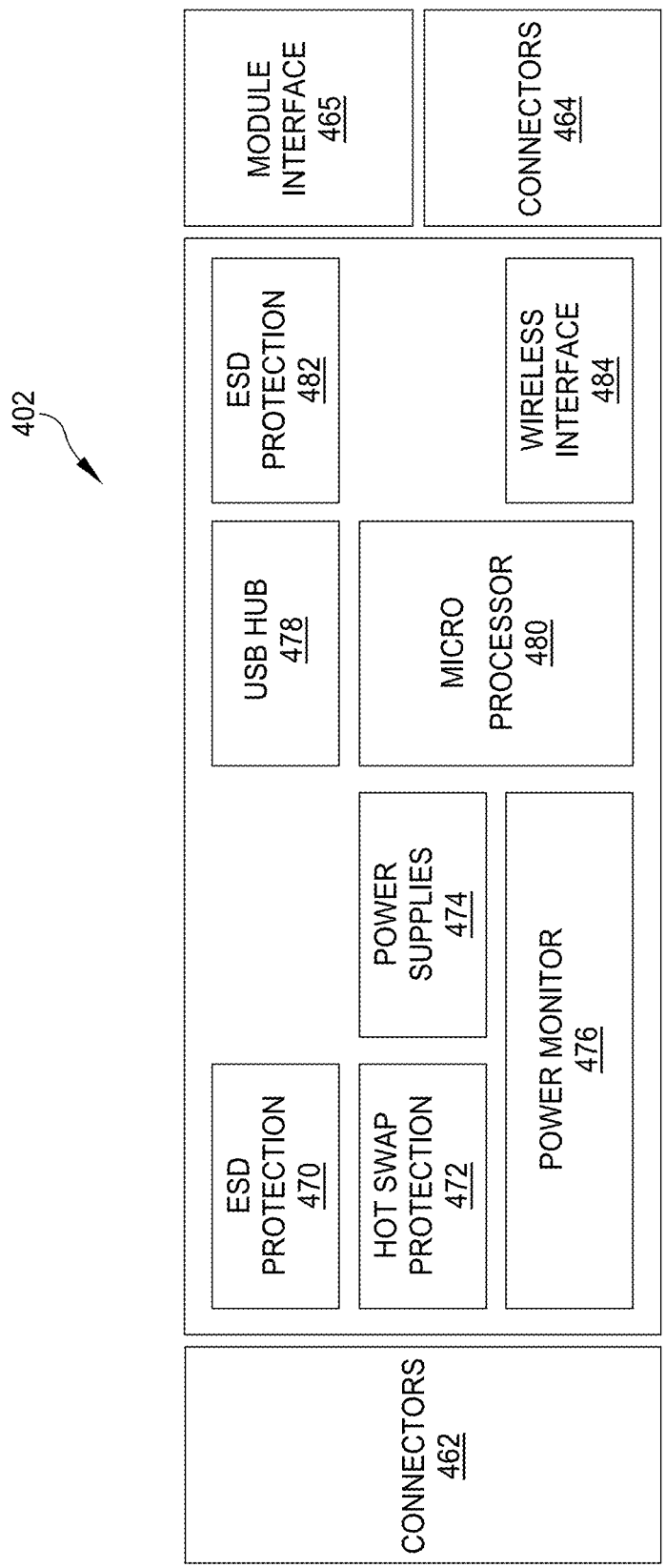
FIG. 4B illustrates a tactical PAN hub.

FIG. 4B illustrates a tactical PAN hub 402. The tactical PAN hub can be used to provide power management, to protect PAN components from over/under voltage, over current, and the like. The tactical PAN hub can control power distribution, power scavenging, etc. The tactical PAN hub is connected to, and functionally supports, a personal area network connection which is preferably built around the aforementioned interconnection laminate substrate. The interconnection laminate substrate may be flexible or rigid. In the preferred form of the invention, the interconnection laminate substrate is flexible. A tactical PAN hub 460 comprises a variety of components, where the components can perform a range of tasks that support, manage, and protect the PAN hub, protect and control the PAN components, etc. The tactical PAN hub can include exposed connectors such as exposed connectors 462, exposed connectors 464, and so on. The exposed connectors can include power connectors, peripheral connectors such as USB connectors, mil-spec connectors, and so on. The tactical PAN hub can include module interfaces 465. The module interfaces can be used to couple wired PAN components, wireless PAN components, etc., to the tactical PAN hub.

The tactical PAN hub can include an electrostatic discharge (ESD) protection component 470. The ESD component can protect the hub from electrostatic discharge that can occur when touching connectors, objects, etc. The tactical PAN hub can include a hot swap protection component 472. The hot swap protection component can protect the hub when plugging or unplugging PAN components into exposed connectors coupled to the hub. The tactical PAN hub can include power supplies 474. The power supplies can be used to convert voltages such as a voltage from a battery to one or more voltages required for operating the one or more PAN components. The PAN hub can include a power monitor 476. The power monitor can be used for power management of one or more PAN components plugged into the tactical PAN hub. In embodiments, the power management can enable or disable power to devices based on previous usage. Devices that are rarely used can be shut down or placed in a lower power mode until needed. In further embodiments, the power management can provide recommendations for device power on or power off. Power management could recommend turning off lighting during daylight hours, powering down a VR or AR headset when not in use or unused for a period of time, etc. In other embodiments, the power management can protect personal area network components and interconnects during overvoltage or over-current conditions.

The tactical PAN hub can include a USB hub 478. The USB hub can enable connecting one or more USB devices to the tactical PAN hub. The USB hub can enable connecting a storage device such as a flash device; an input device such as a keyboard, trackpad, or mouse; an output device such as a printer; and the like. The tactical PAN hub can include a microprocessor 480. The microprocessor can perform operations associated with the tactical PAN hub. The microprocessor can analyze data obtained using one or more sensors, can monitor power usage of PAN components, can apply power management techniques to the operation of PAN components, can recommend powering down or powering up PAN components, etc. The microprocessor can send and receive messages. The tactical PAN hub can include an ESD protection component 482. The ESD protection component can protect the PAN against electrostatic discharge, where the ESD could disrupt components of the tactical PAN hub such as the microprocessor, could damage connectors or input/output circuitry, and the like. The tactical PAN hub can include a wireless interface 484. The wireless interface can enable a wireless connection between a wireless PAN component and the hub. The wireless interface can be based on a variety of wireless protocols or techniques such as Wi-Fi™, Bluetooth™, Zigbee™, infrared, and the like.

FIGS. 5A and 5B show an example tactical personal area network. A user can interact with a variety of electronic components. The electronic components can be used individually or can operate cooperatively. The electronic components can communicate between or among themselves based on a personal area network. The personal area connection uses an interconnection laminate substrate. The interconnection laminate substrate may be flexible or rigid. In the preferred form of the invention, the interconnection laminate substrate is flexible. The interconnection laminate substrate can provide one or more power sources, wired communications paths, wireless communications, and so on. In one form of the invention, a plurality of personal area network components is provided, and an interconnection laminate substrate is provided within a manufactured article (e.g., a soft good assembly). At least one component of the plurality of personal area network components is plugged into at least one exposed connector of the plurality of exposed connectors (i.e., a connection of the interconnection laminate substrate).

An example tactical personal area network configuration is shown at 500. As discussed herein, a personal area network can be based on an interconnection laminate substrate. The interconnection laminate substrate can comprise interconnection wiring encapsulated in one or more protective encapsulation layers and exposed connectors electrically connected to the interconnection wiring. The interconnection laminate substrate can be configured as, incorporated in or mounted to a piece of apparel, a piece of equipment, and so on. The interconnection laminate substrate can be configured as, incorporated in or mounted to a manufactured article (e.g., a soft good assembly). In embodiments, the manufactured article can include a vest, a rucksack, a helmet, a seat, and so on. The interconnection laminate substrate can utilize a variety of materials. In embodiments, the interconnection laminate substrate can include one or more protective encapsulation layers which encapsulate interconnection wiring. The one or more protective encapsulation layers can be a flexible thermoplastic. In the preferred form of the invention, the flexible thermoplastic provides an environmental seal, can be sewn to, can be drilled through or bolted to, etc. In one preferred form of the invention, the flexible thermoplastic comprises a Tegris® thermoplastic composite made by Milliken Textiles of Spartanburg, SC. The flexible thermoplastic can be configured such that it can be incorporated into or inserted into the vest, the rucksack, and so on. The example tactical personal area network connection shown at 500 is in the form of a cummerbund configuration, and can include a pouch, pocket, box, etc., such as shown at 512, into which a power source or other component can be placed. A power source can include a battery such as a sealed lead acid battery, a lithium-ion battery, a lithium-iron-phosphate battery, and the like. In embodiments, the battery can comprise a conformable wearable battery. The power source can further include a power scavenging source. A scavenging source can harvest energy from a renewable energy source, can convert mechanical or thermal energy, and so on. In embodiments, the power scavenging source can derive energy from solar power, body motion, or body heat.

The battery or the power scavenging source can be attached to the interconnection laminate substrate 514. The one or more PAN components can be plugged into the interconnection laminate substrate using an exposed connector 515 which is electrically connected to interconnection wiring encapsulated within the interconnection laminate substrate. The exposed connector can include a commercial connector, a military connector, etc. In embodiments, the exposed connectors can include a cable. In embodiments, the interconnection laminate substrate can be situated in a garment. The garment can be worn alone, under other garments or equipment, over other garments or equipment, etc. In embodiments, the garment can include a vest. The vest can include a tactical vest for military or law enforcement applications, a vest that provides warmth, etc. In further embodiments, the garment can wrap the interconnection laminate substrate around the torso of a wearer. The interconnection laminate substrate can include a belt, a wrap, a rib belt, etc. In embodiments, the garment can include a cummerbund. An example vest or cummerbund configuration is shown at 500. The configuration 500 can include a compartment or pocket 512 for the power source. The configuration 500 can include one or more cables or exposed connectors 524 that can accomplish coupling of the power source to one or more interconnection laminate substrates via the exposed connector 515. The pocket or pouch 512 can include additional components, where the additional components can accomplish wired or wireless communication, power management, etc. In further embodiments, the interconnection laminate substrate can enable the plurality of personal area network components to provide command, control, or communication (CCC) capabilities.

Figure 6B:
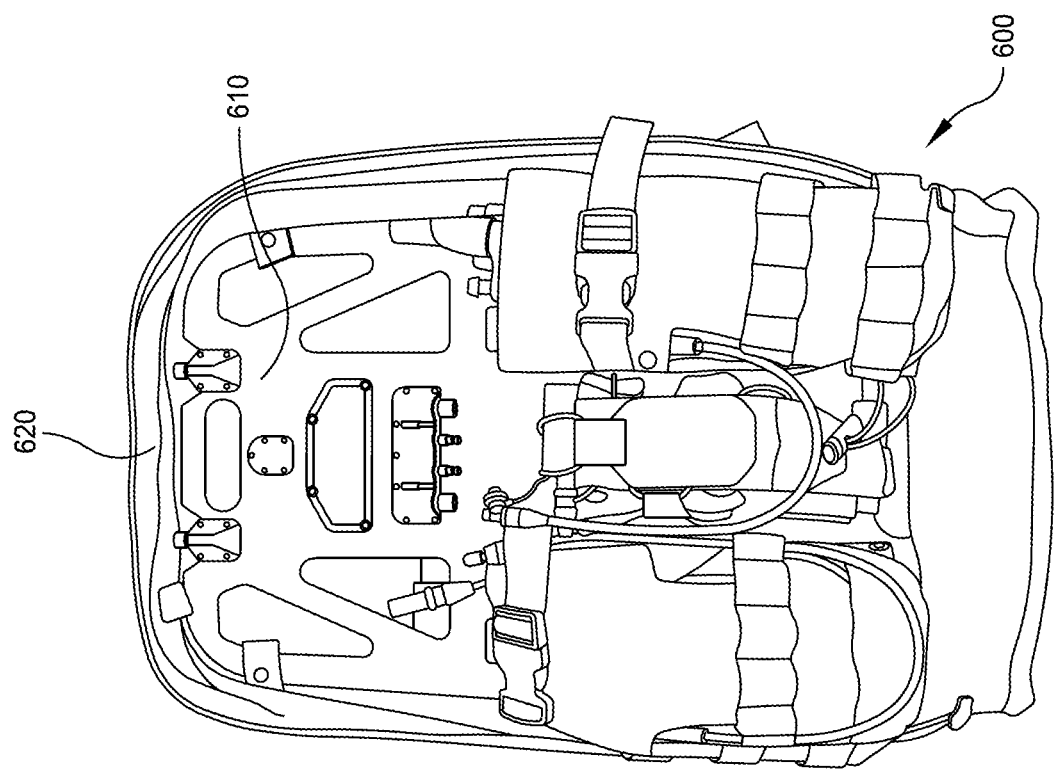
FIGS. 6A and 6B show a personal area network in a rucksack configuration.
Figure 6A:
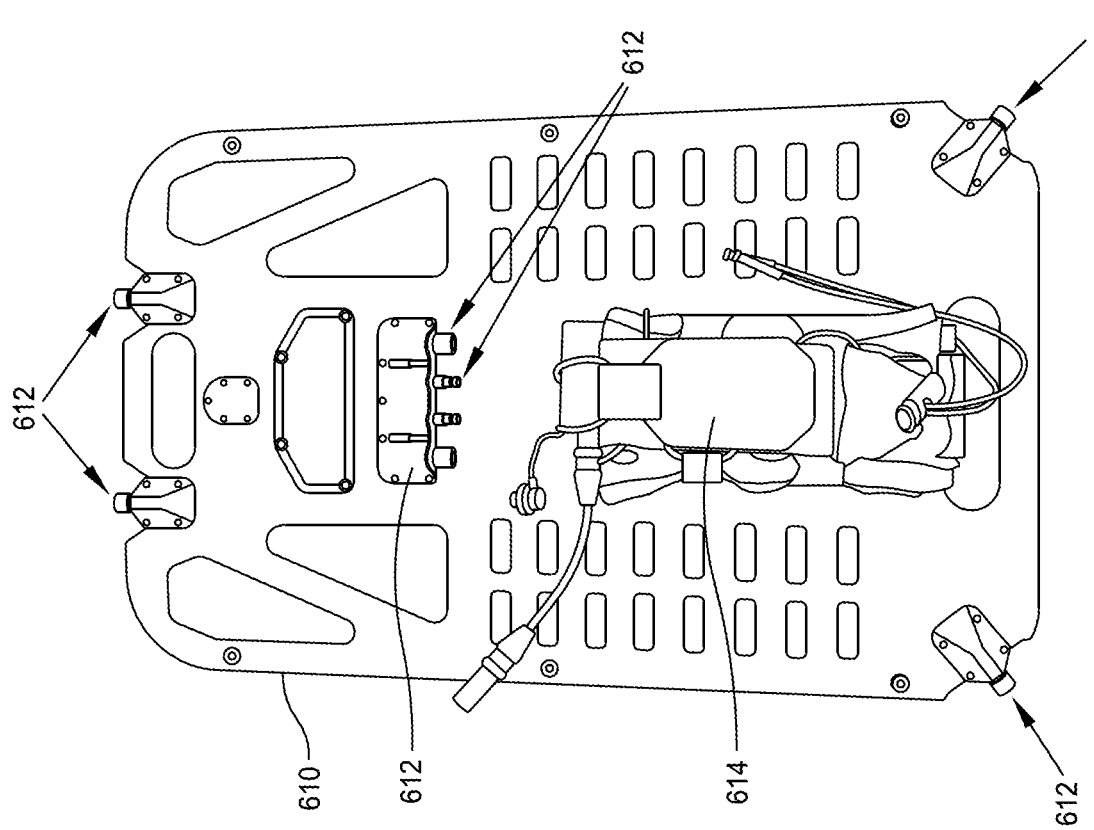

FIGS. 6A and 6B show a tactical personal area network in a rucksack configuration. A personal area network connection scheme can be based on using an interconnection laminate substrate. The interconnection laminate substrate may be flexible or rigid. In the preferred form of the invention, the interconnection laminate substrate is flexible. The interconnection laminate substrate can include a stack-up of various conducting, insulating, shielding, and other layers. The interconnection laminate substrate can include one or more protective encapsulation layers. The one or more protective encapsulation layers can be a flexible thermoplastic. In the preferred form of the invention, the flexible thermoplastic provides an environmental seal, can be sewn to, can be drilled through or bolted to, etc. In one preferred form of the invention, the flexible thermoplastic comprises a Tegris® thermoplastic composite made by Milliken Textiles of Spartanburg, SC. In one form of the invention, a plurality of personal area network components is provided, and an interconnection laminate substrate is provided within a manufactured article (e.g., a soft good assembly such as a rucksack). The interconnection laminate substrate enables connectivity among the plurality of personal area network components, using encapsulated interconnection wiring which is coupled to a plurality of exposed connectors. At least one component of the plurality of personal area network components is plugged into at least one exposed connector of the plurality of exposed connectors.

A tactical personal area network 600 can use an interconnection laminate substrate, where the interconnection laminate substrate can be configured as an item of apparel, a piece of equipment such as a rucksack, and so on. An interconnection laminate substrate is shown at 610. The interconnection laminate substrate can be built into the item of apparel, the piece of equipment such as the rucksack, and so on. The interconnection laminate substrate can be inserted the rucksack, can be removable from the rucksack, etc. The interconnection laminate substrate can include one or more exposed connectors 612. The one or more exposed connectors can include consumer off-the-shelf (COTS) connectors, military standard connectors, and the like. The interconnection laminate substrate can include a compartment 614. The compartment can comprise flexible material, rigid material, etc. The compartment can be used to hold a power source such as a battery. A rucksack 620 is shown, into which the interconnection laminate substrate 610 has been inserted. In other embodiments, the interconnection laminate substrate can be situated in a backpack. At least one component of the plurality of PAN components can be plugged into an exposed connector associated with the interconnection laminate substrate inserted into the rucksack. The at least one PAN component can include components for communication, video, location such as GPS location, power provisioning and management, biometrics for monitoring the user of the rucksack, augmented reality, heated garments such as gloves, haptic feedback components, etc.

Figure 7A:
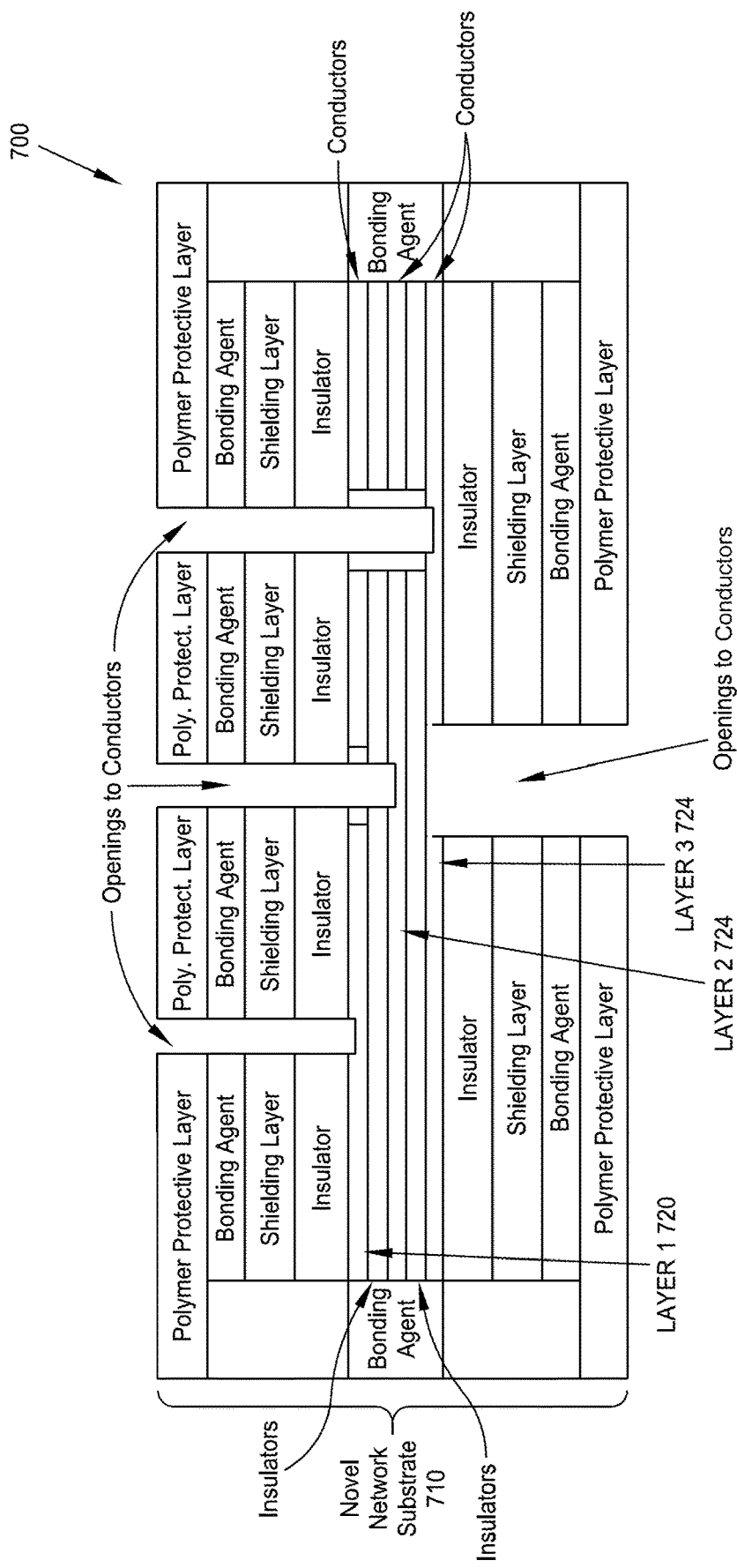
FIGS. 7A and 7B show two exemplary configurations for the interconnection laminate substrate.
Figure 7B:
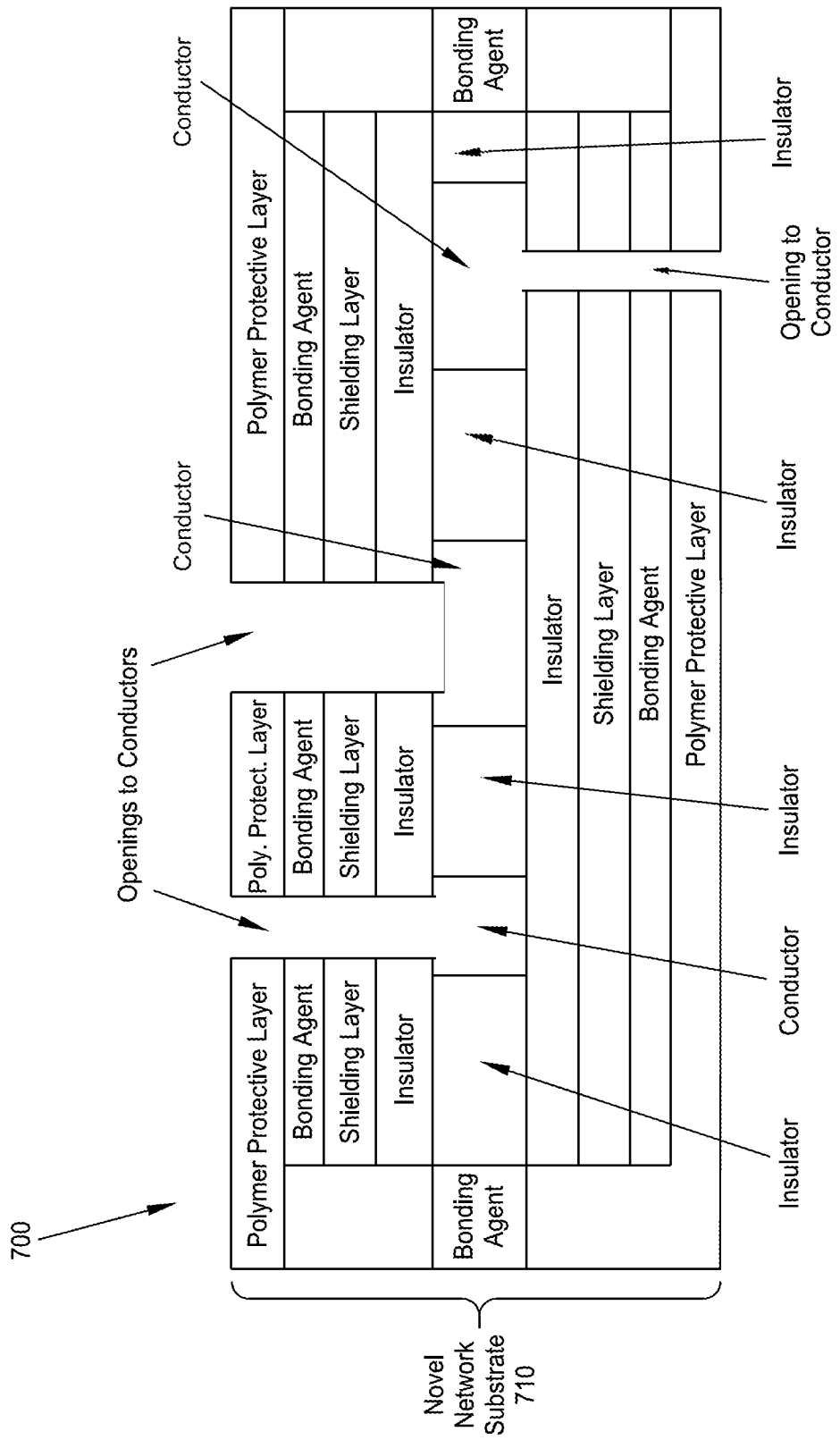

FIGS. 7A and 7B show exemplary interconnection laminate substrates 700. Interconnection laminate substrates 700 may be flexible or rigid. In the preferred forms of the invention, the interconnection laminate substrates 700 are flexible. FIG. 7A shows the encapsulated interconnection wiring (conductors) "stacked" (i.e., distributed) vertically, and FIG. 7B shows the encapsulated interconnection wiring (conductors) "stacked" (i.e., distributed) horizontally. In both cases, the encapsulated interconnection wiring is encased by a protective encapsulation layer, with the different conductors being separated by insulators, and with shield layers being incorporated in the interconnection laminate substrates. As discussed herein, PAN components can be coupled to an interconnection laminate substrate. The coupling can be accomplished using an exposed connector. The stack-up with layers can include layers or laminations of a fabric, a flexible thermoplastic, etc., between or among which shielding layers can be interspersed. The stack-up with shield layers enables personal area network connection using an interconnection laminate substrate. In one form of the invention, a plurality of personal area network components is provided. An interconnection laminate substrate is provided within a manufactured article (e.g., a soft good assembly), where the interconnection laminate substrate enables connectivity among the plurality of personal area network components, and where the interconnection laminate substrate comprises interconnection wiring encapsulated in the interconnection laminate substrate and coupled to a plurality of exposed connectors. At least one component of the plurality of personal area network components is plugged into at least one exposed connector of the plurality of exposed connectors.

Looking now at FIG. 7A, a cross-section of a stack-up with shield layers is shown at 710. The stack-up can be used to provide an interconnection laminate substrate, where the interconnection laminate substrate can enable plugging of PAN components into the interconnection laminate substrate. The interconnection laminate substrate can provide powering capabilities, communications capabilities, and so on. In embodiments, the interconnection laminate substrate comprises a protective encapsulation layer, e.g., a woven thermoplastic. In the preferred form of the invention, the woven thermoplastic provides an environmental seal, can be sewn to, can be drilled through or bolted to, etc. In one preferred form of the invention, the woven thermoplastic comprises a Tegris® thermoplastic composite made by Milliken Textiles of Spartanburg, SC. The stack-up can include various types of layers. The stack-up can include shielding layers, overlay layers, adhesive layers, polyimide layers, conducting layers, and so on. The shielding layers can be used to limit undesirable reception, generation, or propagation, etc., of electromagnetic energy such as electromagnetic signals. The shielding layers can be included to meet emissions requirements such as MIL-STD-461. The overlay layers can enable flexible circuit board connectivity for communication between and among PAN components, control tasks, and the like. The polyimide layers can provide heat-resistance capabilities to the interconnection laminate substrate. The one or more adhesive layers can bind the other layers together into the interconnection laminate substrate. Further layers, such as layer 1 720, layer 2 722, layer 3 724, and so on, can comprise a conductor such as copper. Layer 1 can be used for providing power, where the power can be provided from a source such as a battery; a power scavenging source such as a solar cell, motion converter, or body heat converter; etc. The battery can include a sealed lead acid (SLA) battery, a LiFePO4 battery, etc. In embodiments, the battery can include a conformable wearable battery. Layer 2 can provide communication, controlled impedance communication such as controlled impedance USB communication, and the like. Layer 3 can be used for a ground plane, a ground return path, and so on.

FIG. 7B illustrates another exemplary form of the interconnection laminate substrate 700. The interconnection laminate substrate 700 shown in FIG. 7B is generally similar to the interconnection laminate substrate shown in FIG. 7A, except that the encapsulated interconnection wiring (conductors) are arranged horizontally as opposed to arranged vertically.

Figure 8:
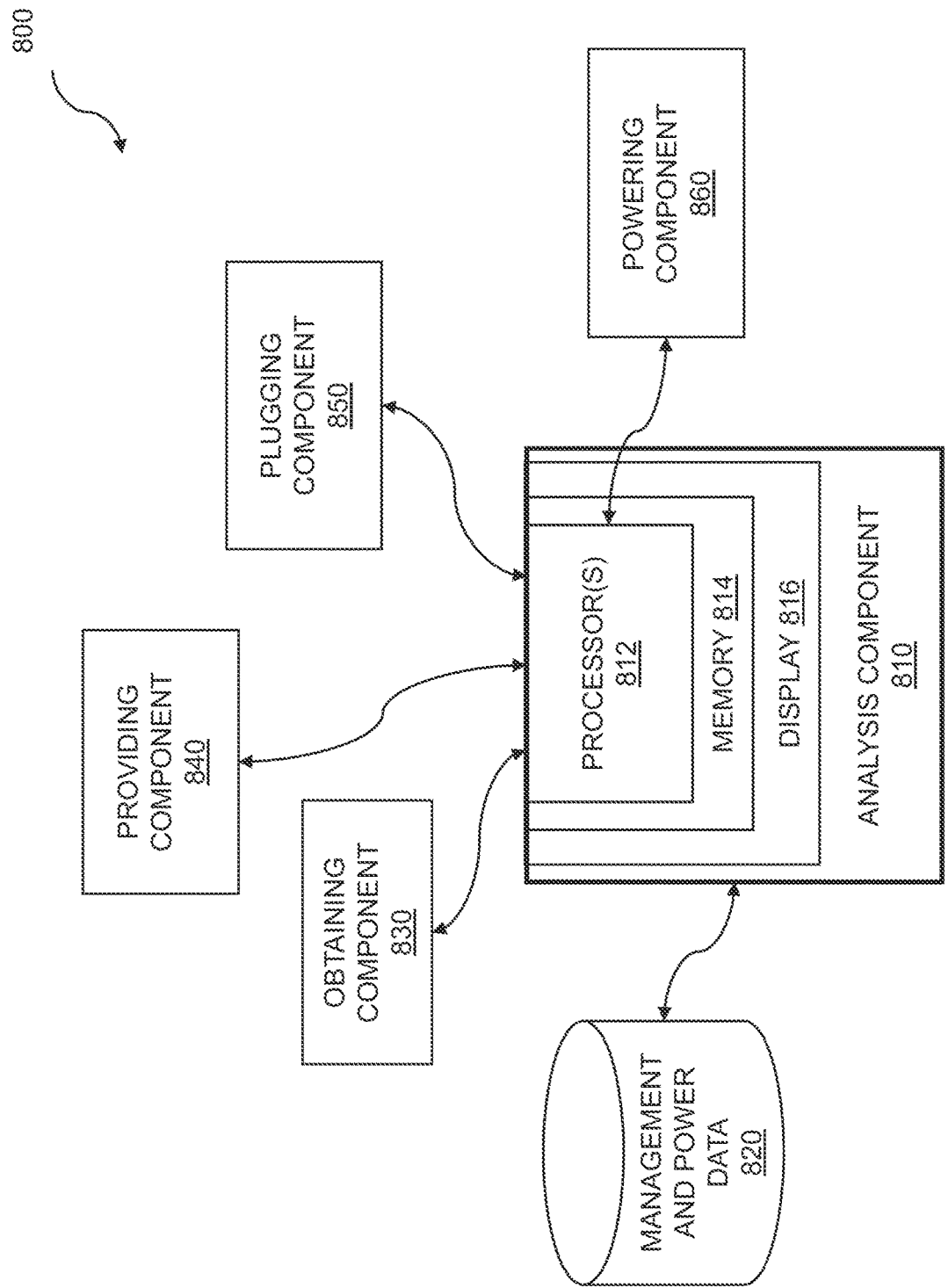
FIG. 8 is a system diagram for a personal area network connection using an interconnection laminate substrate.

FIG. 8 is a system diagram for personal area network connection using an interconnection laminate substrate. The interconnection laminate substrate may be flexible or rigid. In the preferred form of the invention, the interconnection laminate substrate is flexible. Personal area network (PAN) components can be plugged into exposed connectors coupled to a flexible garment such as a vest or other soft good. The personal area network connection uses an interconnection laminate substrate. In one form of the invention, an interconnection laminate substrate with encapsulated interconnection wiring and exposed connectors is provided. At least one component can be plugged into one of the exposed connectors. Power can be provided to the PAN component using a power source such as a battery or a power scavenging source. The power scavenging source can derive energy from solar power, body motion, or body heat.

The system 800 can include an analysis component 810. The analysis component can include one or more electronic components which can be used to monitor and control one or more personal area network components coupled to an interconnection laminate substrate. The analysis component 810 can comprise one or more processors 812, a memory 814 coupled to the one or more processors 812, and a display 816. The display 816 can be configured and disposed to present collected data, analysis, intermediate analysis steps, instructions, algorithms, heuristics, a power usage signature, power source status data, and so on.

The system 800 can include a management component and power data 820. The management data can include a library of lookup tables, power usage characteristics, power source charging characteristics, functions, algorithms, routines, code segments, apps, and so on, that can be used for management of power to one or more personal area network components. The power data can include status of a source of electrical power, power dissipation data for the PAN component, and so on. The system 800 can include an obtaining component 830. The obtaining component can obtain a plurality of personal area network components that can be coupled to the analysis component 810. The obtaining component can further provide data associated with operating the obtained PAN components. The data associated with the PAN components can include power usage requirements such as maximum operating power, standby power, and so on. The data can further include a priority for the PAN component. The obtained PAN component can include a communications or processing component, a navigation component, a health monitoring component, a heating component, and so on. The obtained PAN component can include a power source.

The system 800 can include a providing component 840. The providing component can provide an interconnection laminate substrate within a manufactured article (e.g., a soft good assembly). The manufactured article can include a garment such as a vest or cummerbund, a hat, gloves, socks, and so on. The interconnection laminate substrate can enable connectivity among the plurality of personal area network components. The connectivity can enable power distribution, communication, control, and the like. The interconnection laminate substrate can comprise encapsulated interconnection wiring coupled to a plurality of exposed connectors. The encapsulated interconnection wiring can include a wiring layer within the interconnection laminate substrate, conducting fibers, wires, cables, and so on. The exposed connectors can include consumer off-the-shelf (COTS) connectors, proprietary connectors, mil-spec connectors, etc. The providing component can provide power to the PAN components, scavenge power, and the like. The system 800 can include a plugging component 850. The plugging component can enable plugging at least one component of the plurality of personal area network components into at least one exposed connector of the plurality of exposed connectors. The plugging component can enable unplugging a PAN component to replace the PAN component with a substantially similar component or a different component.

The system 800 can include a powering component 860. The powering component can enable powering the at least one component, where the powering is enabled by the plugging. The powering component can include an energy source plugged into the substrate. The energy source can include a battery such as a sealed lead acid (SLA) battery, a lithium-ion battery, a lithium-iron-phosphate (LiFePO4) battery, and so on. The energy source can include a power scavenging source. The power scavenging source can capture or "scavenge" power, where the power can include renewable power, power generated by a person wearing or using the manufactured article (e.g., a soft good assembly such as a garment), and the like. The power scavenging source can derive energy from solar power using one or more solar cells, where the solar cells can be coupled to or embedded within the manufactured article (e.g., a soft good); using body motion, where the body motion can include movement of arms, legs, or torso, etc.; using body heat, where the body heat can be generated by walking, jogging, running, etc.

The system 800 can include a computer program product embodied in a non-transitory computer readable medium for personal area network enablement, the computer program product comprising code which causes one or more processors to perform desired operations.

Each of the above methods may be executed on one or more processors on one or more computer systems. Embodiments may include various forms of distributed computing, client/server computing, and cloud-based computing. Further, it will be understood that the depicted steps or boxes contained in this disclosure's flow charts are solely illustrative and explanatory. The steps may be modified, omitted, repeated, or re-ordered without departing from the scope of this disclosure. Further, each step may contain one or more sub-steps. While the foregoing drawings and description set forth functional aspects of the disclosed systems, no particular implementation or arrangement of software and/or hardware should be inferred from these descriptions unless explicitly stated or otherwise clear from the context. All such arrangements of software and/or hardware are intended to fall within the scope of this disclosure.

The block diagrams and flowchart illustrations depict methods, apparatus, systems, and computer program products. The elements and combinations of elements in the block diagrams and flow diagrams, show functions, steps, or groups of steps of the methods, apparatus, systems, computer program products and/or computer-implemented methods. Any and all such functions—generally referred to herein as a "circuit," "module," or "system"—may be implemented by computer program instructions, by special-purpose hardware-based computer systems, by combinations of special purpose hardware and computer instructions, by combinations of general purpose hardware and computer instructions, and so on.

A programmable apparatus which executes any of the above-mentioned computer program products or computer-implemented methods may include one or more microprocessors, microcontrollers, embedded microcontrollers, programmable digital signal processors, programmable devices, programmable gate arrays, programmable array logic, memory devices, application specific integrated circuits, or the like. Each may be suitably employed or configured to process computer program instructions, execute computer logic, store computer data, and so on.

It will be understood that a computer may include a computer program product from a computer-readable storage medium and that this medium may be internal or external, removable and replaceable, or fixed. In addition, a computer may include a Basic Input/Output System (BIOS), firmware, an operating system, a database, or the like that may include, interface with, or support the software and hardware described herein.

Embodiments of the present invention are neither limited to conventional computer applications nor the programmable apparatus that run them. To illustrate: the embodiments of the presently claimed invention could include an optical computer, quantum computer, analog computer, or the like. A computer program may be loaded onto a computer to produce a particular machine that may perform any and all of the depicted functions. This particular machine provides a means for carrying out any and all of the depicted functions.

Any combination of one or more computer readable media may be utilized including but not limited to: a non-transitory computer readable medium for storage; an electronic, magnetic, optical, electromagnetic, infrared, or semiconductor computer readable storage medium or any suitable combination of the foregoing; a portable computer diskette; a hard disk; a random access memory (RAM); a read-only memory (ROM), an erasable programmable read-only memory (EPROM, Flash, MRAM, FeRAM, or phase change memory); an optical fiber; a portable compact disc; an optical storage device; a magnetic storage device; or any suitable combination of the foregoing. In the context of this document, a computer readable storage medium may be any tangible medium that can contain or store a program for use by or in connection with an instruction execution system, apparatus, or device.

It will be appreciated that computer program instructions may include computer executable code. A variety of languages for expressing computer program instructions may include without limitation C, C++, Java, JavaScript™, ActionScript™, assembly language, Lisp, Perl, Tcl, Python, Ruby, hardware description languages, database programming languages, functional programming languages, imperative programming languages, and so on. In embodiments, computer program instructions may be stored, compiled, or interpreted to run on a computer, a programmable data processing apparatus, a heterogeneous combination of processors or processor architectures, and so on. Without limitation, embodiments of the present invention may take the form of web-based computer software, which includes client/server software, software-as-a-service, peer-to-peer software, or the like.

In embodiments, a computer may enable execution of computer program instructions including multiple programs or threads. The multiple programs or threads may be processed approximately simultaneously to enhance utilization of the processor and to facilitate substantially simultaneous functions. By way of implementation, any and all methods, program codes, program instructions, and the like described herein may be implemented in one or more threads which may in turn spawn other threads, which may themselves have priorities associated with them. In some embodiments, a computer may process these threads based on priority or other order.

Unless explicitly stated or otherwise clear from the context, the verbs "execute" and "process" may be used interchangeably to indicate execute, process, interpret, compile, assemble, link, load, or a combination of the foregoing. Therefore, embodiments that execute or process computer program instructions, computer-executable code, or the like may act upon the instructions or code in any and all of the ways described. Further, the method steps shown are intended to include any suitable method of causing one or more parties or entities to perform the steps. The parties performing a step, or portion of a step, need not be located within a particular geographic location or country boundary. For instance, if an entity located within the United States causes a method step, or portion thereof, to be performed outside of the United States then the method is considered to be performed in the United States by virtue of the causal entity.

While the invention has been disclosed in connection with preferred embodiments shown and described in detail, various modifications and improvements thereon will become apparent to those skilled in the art. Accordingly, the foregoing examples should not limit the spirit and scope of the present invention; rather it should be understood in the broadest sense allowable by law.

What is claimed is:

1. A method for personal area network enablement, the method comprising:
   providing a plurality of personal area network components;
   providing a laminated soft good assembly comprising an integrated electrical distribution substrate for integration of at least one of power lines and data signals within the laminated soft good assembly;
   wherein the laminated soft good assembly comprising the electrical distribution substrate enables connectivity among the plurality of personal area network components, and wherein the electrical distribution substrate comprises:
   flex circuitry or flex conductors encapsulated in at least one protective encapsulation layer; and
   a plurality of exposed connectors disposed on at least one of a top surface and a bottom surface of the electrical distribution substrate,
   wherein the encapsulated flex circuitry or flex conductors are coupled to the plurality of exposed connectors; and
   connecting at least one component of the plurality of personal area network components into at least one exposed connector of the plurality of the exposed connectors.

2. A method according to claim 1 wherein the laminated soft good assembly is flexible.

3. A method according to claim 1 wherein the at least one protective encapsulation layer provides an environmental seal for the encapsulated flex circuitry or flex conductors contained within the electrical distribution substrate.

4. A method according to claim 1 wherein the at least one protective encapsulation layer provides mechanical protection for the encapsulated flex circuitry or flex conductors contained within the electrical distribution substrate.

5. A method according to claim 1 wherein the laminated soft good assembly can be sewn to, can be drilled through, or can be bolted to.

6. A method according to claim 1 wherein the at least one protective encapsulation layer comprises a polymer.

7. A method according to claim 6 wherein the polymer comprises a thermoplastic.

8. A method according to claim 7 wherein the thermoplastic comprises a woven thermoplastic material.

9. A method according to claim 8 wherein the woven thermoplastic material comprises Tegris®.

10. A method according to claim 1 wherein the laminated soft good assembly comprises a hub for data distribution.

11. A method according to claim 1 wherein the encapsulated flex circuitry or flex conductors comprises a plurality of conductors separated by insulators.

12. A method according to claim 11 wherein the plurality of conductors are stacked vertically.

13. A method according to claim 11 wherein the plurality of conductors are arranged horizontally.

14. A method according to claim 1 wherein the electrical distribution substrate comprises electromagnetic interference (EMI) shielding encapsulated in the at least one protective encapsulation layer.

15. A method according to claim 1 wherein the personal area network components comprise at least one electronic device.

16. A method according to claim 15 wherein the at least one electronic device comprises at least one from the group consisting of a power management hub, a radio, a video downlink device, a GPS device, a laser rangefinder, a biometric sensor, a haptic feedback device, a gesture glove, a heads up display, a cooling system and a heated apparel system.

17. A method according to claim 1 wherein the laminated soft good assembly comprises at least one from the group consisting of a garment, a backpack, a rucksack, a helmet, a seat and a seatback.

18. A method according to claim 17 wherein the garment comprises a vest.

19. A method according to claim 18 wherein the vest includes a cummerbund.

20. A method according to claim 1 wherein the laminated soft good assembly comprises a cummerbund of a vest.

21. A method according to claim 1 wherein the personal area network components comprise at least one body sensor.

22. A method according to claim 21 wherein the at least one body sensor comprises at least one from the group consisting of a blood oxygen sensor, an orientation sensor, an acceleration sensor, a heart rate sensor, and a body temperature sensor.

23. A method according to claim 1 further comprising powering at least one of the plurality of personal area network components.

24. A method according to claim 23 wherein powering uses an energy source connected to the laminated soft good assembly.

25. A method according to claim 24 wherein the energy source comprises a battery.

26. A method according to claim 25 wherein the battery comprises a conformable wearable battery.

27. A method according to claim 24 wherein the energy source comprises a power scavenging source.

28. A method according to claim 27 wherein the power scavenging source derives energy from at least one from the group consisting of solar power, body motion, and body heat.

29. A method according to claim 23 wherein the powering is controlled by power management.

30. A method according to claim 29 wherein the power management enables or disables power to devices based on previous usage.

31. A method according to claim 29 wherein the power management provides recommendations for device power on or device power off.

32. A method according to claim 29 wherein the power management protects the plurality of personal area network components and the flex circuitry or flex conductors during over-voltage or over-current conditions.

33. A method according to claim 1 wherein the laminated soft good assembly comprises a portion of a rucksack.

34. A method according to claim 1 wherein the laminated soft good assembly comprises at least one from the group consisting of a buckle, a hook and loop fastener, a zipper and a button.

35. Apparatus for personal area network enablement, the apparatus comprising:
a plurality of personal area network components; and
a laminated soft good assembly comprising an integrated electrical distribution substrate for integration of at least one of power lines and data signals within the laminated soft good assembly;
wherein the laminated soft good assembly comprising the electrical distribution substrate enables connectivity among the plurality of personal area network components, and wherein the electrical distribution substrate comprises:
flex circuitry or flex conductors encapsulated in at least one protective encapsulation layer; and
a plurality of exposed connectors disposed on at least one of a top surface and a bottom surface of the electrical distribution substrate; and
wherein a first of the plurality of personal area network components is connected to a first of the plurality of exposed connectors, and a second of the plurality of personal area network components is connected to a second of the plurality of exposed connectors.

36. An apparatus according to claim 35 wherein the at least one protective encapsulation layer provides mechanical protection for the flex circuitry or flex conductors contained within the electrical distribution substrate.

37. An apparatus according to claim 35 wherein the laminated soft good assembly can be sewn to, can be drilled through, or can be bolted to.

38. An apparatus according to claim 35 wherein the at least one protective encapsulation layer comprises a polymer.

39. An apparatus according to claim 38 wherein the polymer comprises a thermoplastic.

40. An apparatus according to claim 39 wherein the thermoplastic comprises a woven thermoplastic material.

41. An apparatus according to claim 40 wherein the woven thermoplastic material comprises Tegris®.

42. An apparatus according to claim 35 wherein the laminated soft good assembly is flexible.

43. An apparatus according to claim 35 wherein the flex circuitry or flex conductors comprises a plurality of conductors separated by insulators.

44. An apparatus according to claim 43 wherein the plurality of conductors are stacked vertically.

45. An apparatus according to claim 43 wherein the plurality of conductors are arranged horizontally.

46. An apparatus according to claim 35 wherein the electrical distribution substrate comprises electromagnetic interference (EMI) shielding encapsulated in the at least one protective encapsulation layer.

47. An apparatus according to claim 35 wherein the laminated soft good assembly comprises a hub for data distribution.

48. An apparatus according to claim 35 wherein the laminated soft good assembly comprises a cummerbund of a vest.

49. An apparatus according to claim 35 wherein the laminated soft good assembly comprises at least one from the group consisting of a garment, a backpack, a rucksack, a helmet, a seat and a seatback.

50. An apparatus according to claim 49 wherein the garment comprises a vest.

51. An apparatus according to claim 50 wherein the vest includes a cummerbund.

52. An apparatus according to claim 35 wherein the at least one protective encapsulation layer provides an environmental seal for the flex circuitry or flex conductors contained within the electrical distribution substrate.

53. An apparatus according to claim 35 wherein the personal area network components comprise at least one body sensor.

54. An apparatus according to claim 53 wherein the at least one body sensor comprises at least one from the group consisting of a blood oxygen sensor, an orientation sensor, an acceleration sensor, a heart rate sensor, and a body temperature sensor.

55. An apparatus according to claim 35 wherein the at least one of the plurality of personal area network components are configured to receive power.

56. An apparatus according to claim 55 wherein powering uses an energy source connected to the laminated soft good assembly.

57. An apparatus according to claim 56 wherein the energy source comprises a battery.

58. An apparatus according to claim 57 wherein the battery comprises a conformable wearable battery.

59. An apparatus according to claim 56 wherein the energy source comprises a power scavenging source.

60. An apparatus according to claim 59 wherein the power scavenging source derives energy from at least one from the group consisting of solar power, body motion, and body heat.

61. An apparatus according to claim 55 wherein the powering is controlled by power management.

62. An apparatus according to claim 61 wherein the power management enables or disables power to devices based on previous usage.

63. An apparatus according to claim 61 wherein the power management provides recommendations for device power on or device power off.

64. An apparatus according to claim 61 wherein the power management protects the plurality of personal area network components and the flex circuitry or flex conductors during over-voltage or over-current conditions.

65. An apparatus according to claim 35 wherein the laminated soft good assembly comprises a portion of a rucksack.

66. An apparatus according to claim 35 wherein the laminated soft good assembly comprises at least one of a buckle, a hook and loop fastener, a zipper and a button.

67. An apparatus according to claim 35 wherein the personal area network components comprise at least one electronic device.

68. An apparatus according to claim 67 wherein the at least one electronic device comprises at least one from the group consisting of a power management hub, a radio, a video downlink device, a GPS device, a laser rangefinder, a biometric sensor, a haptic feedback device, a gesture glove, a heads up display, a cooling system and a heated apparel system.

* * * * *